(12) United States Patent
Chang et al.

(10) Patent No.: US 9,797,763 B2
(45) Date of Patent: Oct. 24, 2017

(54) MEASUREMENT DEVICE FOR DETECTING MATERIAL LEVEL AND TEMPERATURE

(71) Applicant: FINETEK CO., LTD., New Taipei (TW)

(72) Inventors: Liang-Chi Chang, New Taipei (TW); Teng-Chin Yu, New Taipei (TW); Kai-Di Yang, New Taipei (TW); Ting-Kuo Wu, New Taipei (TW); Chao-Kai Cheng, New Taipei (TW)

(73) Assignee: Finetek Co., Ltd., New Taipei (TW)

( * ) Notice: Subject to any disclaimer, the term of this patent is extended or adjusted under 35 U.S.C. 154(b) by 525 days.

(21) Appl. No.: 14/178,341

(22) Filed: Feb. 12, 2014

(65) Prior Publication Data

US 2015/0134278 A1 May 14, 2015

(30) Foreign Application Priority Data

Nov. 12, 2013 (TW) .............................. 102140990 A

(51) Int. Cl.
| | | |
|---|---|---|
| *G01F 23/284* | (2006.01) | |
| *G01N 27/22* | (2006.01) | |
| *G01K 13/10* | (2006.01) | |
| *G01K 1/02* | (2006.01) | |

(52) U.S. Cl.
CPC ........... *G01F 23/284* (2013.01); *G01K 1/026* (2013.01); *G01K 13/10* (2013.01); *G01N 27/22* (2013.01); *G01N 27/228* (2013.01)

(58) Field of Classification Search
CPC ...... G01F 23/284; G01F 23/248; G01F 23/22; G01F 23/268; G01F 23/0069; G01F 15/068; G01K 1/026; G01K 13/10; G01K 7/34; G01N 27/223; G01N 27/22; G01N 27/228
See application file for complete search history.

(56) References Cited

U.S. PATENT DOCUMENTS

| | | | |
|---|---|---|---|
| 6,744,390 B1* | 6/2004 | Stice | H03M 1/129 341/120 |
| 8,950,255 B2* | 2/2015 | Chang | G01F 23/248 73/292 |
| 9,322,717 B1* | 4/2016 | Dhaliwal | G01K 7/00 |
| 2011/0270542 A1* | 11/2011 | Chappell | G01F 23/0076 702/55 |
| 2012/0139565 A1* | 6/2012 | Ambuter | G01N 27/048 324/694 |
| 2013/0106411 A1* | 5/2013 | Chen | G01R 33/18 324/252 |
| 2013/0182742 A1* | 7/2013 | Chang | G01F 23/248 374/142 |

* cited by examiner

*Primary Examiner* — Leslie J Evanisko
*Assistant Examiner* — Leo T Hinze

(57) ABSTRACT

A measurement device for detecting a material level and a temperature has a cable, a level sensing module, a thermal sensing module, a processing module, and a power module. The measurement device detects difference of currents between an electrode of the cable and the earth, and calculates a material level of a material stored in a silo according to the RF admittance. The cable comprises a plurality of thermal sensing units for detecting a temperature of the material. The measurement device further calibrates a material capacitance of the material with the temperature for avoiding an error caused by an inaccurate parameter.

15 Claims, 5 Drawing Sheets

MEASUREMENT DEVICE FOR DETECTING MATERIAL LEVEL AND TEMPERATURE

BACKGROUND OF THE INVENTION

1. Field of the Invention

The present invention relates to a measurement device, and particularly to a measurement device for simultaneously detecting material level and temperature.

2. Description of the Related Art

For management of bulk material stored in a silo, a measurement device for detecting material level is very important. The material level means a height of the material in the silo, and the material level can be converted to obtain the amount of the material stored in the silo. The measurement device can be applied to petrochemical industry, food industry, feed industry, steel industry, cement industry, etc. Materials stored in a silo may be solid, liquid, or liquid-solid mixture. For example, the materials may be petroleum, coal, iron sand, cement, flour, cattle fat, etc. When each material is stored in a silo, temperature, moisture and an amount of the material will influence the quality of the materials. In some particular industries, when the temperature of the material stored in the silo is not properly controlled, a dry and dusty material may cause a dust explosion.

A conventional measurement device can only detect temperature, moisture, or material level of the material. When a user wants to simultaneously detect the temperature, moisture and material level, the user needs to build a system composed of multiple measurement devices for respectively sensing the temperature, the moisture, and the material level. Then the user can monitor the temperature, the moisture and the material level of the material stored in the silo.

Furthermore, the measurement device can detect the material level by radio frequency (RF) admittance. The measurement device provides a particular voltage to an electrode of the measurement device and detects difference of currents between the electrode and the earth caused by material capacitance. Then the measurement device can calculate the material level by the RF admittance according to a known dielectric constant of the material and the difference of currents between the electrode and the earth.

The dielectric constant of material will change with the temperature of the material. Different temperatures of the material correspond to different dielectric constants respectively. The dielectric constant can be converted to the material capacitance. The material capacitance is an important parameter when calculating the material level by the RF admittance. If the material capacitance of the material is not correct, a calculation of the material level by the RF admittance will have an error. Therefore, the measurement device needs to be further improved.

SUMMARY OF THE INVENTION

An objective of the present invention is to provide a measurement device for detecting a material level and a temperature. The measurement device can simultaneously measure the temperature and the material level of a material stored in a silo. The measurement device determines a dielectric constant and material capacitance, and further calibrates the material capacitance according to the temperature of the material. The measurement device calculates the material level by the RF admittance.

To achieve the foregoing objective, the measurement device comprises a cable, a level sensing module, a thermal sensing module, a processing module, and a power module.

The cable comprises an electrode and a plurality of thermal sensing units. The thermal sensing units are mounted on the cable and separated form each other.

The level sensing module is electronically connected with the electrode, outputs a wave signal to the electrode for generating the RF admittance, and further outputs a level signal.

The thermal sensing module is electronically connected with each thermal sensing unit, and outputs a thermal signal.

The processing module comprises a storage unit and a processor. The storage unit is electronically connected with the processor and stores a reference table. The reference table comprises temperatures and material capacitance of the material. The processor is electronically connected with the level sensing module and the thermal sensing module for receiving the level signal and the thermal signal. The processor loads in the reference table, and searches for a material capacitance from the reference table according to the thermal signal received. Then, the processor calculates the material level by the RF admittance.

The power module is electronically connected to the cable, the level sensing module, the thermal sensing module, and the processing module for providing electric power.

The measurement device can detect the difference of currents between the electrode and the earth and calculate the material level according to the difference and the RF admittance. The thermal sensing units are mounted on the cable, and separated from each other. The thermal sensing units detect temperatures alongside the cable. A user can determine the temperature of the silo, and control the temperature at an appropriate temperature for storing the material.

The reference table is saved in the storage unit. The reference table records relationships between the material capacitances and the temperatures. The material capacitance is an important parameter when calculating the material level by the RF admittance. The material capacitance changes with the temperature of the material. Therefore, the processor calibrates the material capacitance according to the temperature and the reference table. Then, the processor calculates the material level according to the calibrated material capacitance and the RF admittance.

Other objectives, advantages and novel features of the invention will become more apparent from the following detailed description when taken in conjunction with the accompanying drawings.

DETAILED DESCRIPTION OF THE INVENTION

Figure 1:
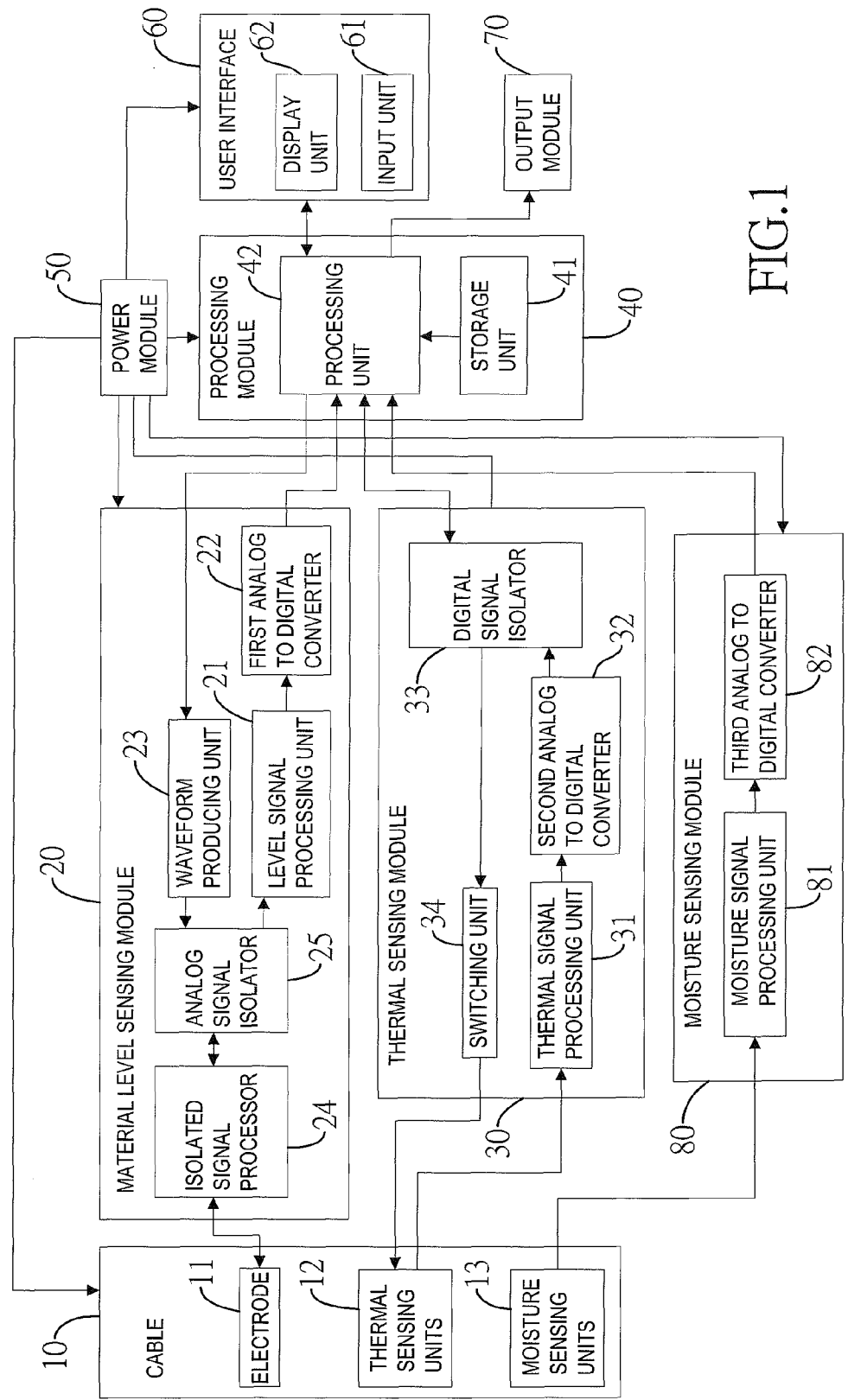
FIG. 1 is a block diagram of an embodiment of a measurement device for detecting a material level and a temperature.

With reference to FIG. 1, the present invention provides a measurement device for detecting a material level and a temperature. In an embodiment of the present invention, the measurement device comprises a cable 10, a level sensing module 20, a thermal sensing module 30, a processing module 40 and a power module 50.

The cable 10 comprises an electrode 11 and a plurality of thermal sensing units 12. The thermal sensing units 12 are mounted on the cable 10 and separated from each other. In the embodiment, the electrode 11 is comprised of steel wire ropes for transmitting signals. The steel wire ropes can further avoid damage caused by impact.

The level sensing module 20 comprises a level signal processor 21, a first analog to digital converter (ADC) 22, and a waveform producing unit 23. The level signal processor 21 is electronically connected between the electrode 11 and the first ADC 22. The level signal processor 21 receives a level signal output by the electrode 11, converts the level signal to an analog level signal, and then transmits the analog level signal to the first ADC 22. The first ADC 22 converts the analog level signal to a digital level signal and outputs the digital level signal. The waveform producing unit 23 is electronically connected between the electrode 11 and the processing module 40. The waveform producing unit 23 produces a wave signal with a specific frequency according to a control signal output by the processing module 40, and outputs the wave signal to the electrode 11 for detecting the material level by the RF admittance.

The thermal sensing module 30 comprises a thermal signal processor 31 and a second ADC 32. The thermal signal processor 31 is electronically connected between the thermal sensing units 12 and the second ADC 32. The thermal signal processor 31 receives thermal signals output by the thermal sensing units 12, and converts the thermal signals to analog thermal signals. The second ADC 32 converts the analog thermal signals to digital thermal signals and outputs the digital thermal signals. In the embodiment, the thermal sensing units 12 may be one-wire digital thermometers, resistance thermometers (RTDs), or thermocouples.

The processing module 40 comprises a storage unit 41 and a processor 42. The storage unit 41 is electronically connected to the processor 42 and saves a reference table. The reference table records relationships between the temperatures and the material capacitances. The processor 42 is electronically connected to the waveform producing unit 23, the first ADC 22 and the second ADC 32 for receiving the digital level signal and the digital thermal signals. The processor 42 determines material capacitance according to the digital level signal. Then the processor 42 refers to the reference table to calibrate the material capacitance based on the digital thermal signals. Therefore, the processor 42 can calculate the material level by the RF admittance according to the calibrated material capacitance and the digital level signal. In the embodiment, the processor 42 is electronically connected with the thermal sensing units 12 through the Modbus protocol by a data input/output 1-wire interface pin.

The power module 50 is electronically connected with the cable 10, the level sensing module 20, the thermal sensing module 30 and the processing module 40 for providing electric power.

The level sensing module 20 further comprises an isolated signal processor 24 and an analog signal isolator 25. The isolated signal processor 24 is electronically connected between the level signal processor 21 and the electrode 11 for removing noise from the level signals to prevent an error. The analog signal isolator 25 is electronically connected between the isolated signal processor 24 and the level signal processor 21, and is further electronically connected to the waveform producing unit 23 for preventing a damage caused by a surge voltage.

The thermal sensing module 30 further comprises a digital signal isolator 33 and a switching unit 34. The digital signal isolator 33 is electronically connected between the second ADC 32 and the processor 42 for preventing a damage caused by the surge voltage. The switching unit 34 is electronically connected between the thermal sensing units 12 and the digital signal isolator 33. The switching unit 34 receives an adjusting signal and adjusts a range of an analog to digital conversion. In the embodiment, the thermal signal processor 31, the second ADC 32, the digital signal isolator 33 can be integrated into a chip for making a fabrication of the present invention easier and further reducing volume of the present invention.

The measurement device further comprises a user interface 60, an output module 70 and a moisture sensing module 80. The user interface 60 is electronically connected to the processor 42 and comprises a display unit 61 and an input unit 62. The display unit 61 displays information such as the temperature of the material or the material level. The input unit 62 is provided to a user for selecting the information displayed on the display unit 61. In the embodiment, the display unit 61 may be a touch panel.

The output module 70 is electronically connected to the processor 42 for receiving signals and output the signals to another electronic device. In the embodiment, the output module 70 may be the RS-232 of the USB interface.

The cable 10 further comprises a plurality of moisture sensing units 13. The moisture sensing units 13 are mounted on the cable 10, and separated from each other for detecting moisture of the material. The moisture sensing module 80 comprises a moisture signal processor 81 and a third ADC 82. The moisture signal processor 81 is electronically connected between the moisture sensing units 13 and the third ADC 82 for receiving moisture signals. The moisture signal processor 81 converts the moisture signals to analog moisture signals. The third ADC 82 is electronically connected to the processor 42. The third ADC 82 converts the analog moisture signals to digital moisture signals, and then outputs the digital moisture signals to the processor 42.

A comparison table is also saved in the storage unit 41. The comparison table records relationships between the moistures and the material capacitances. The processor 42 is further electronically connected to the third ADC 82 for receiving the digital moisture signals. The processor 42 loads in the comparison table. Then, the processor 42 calibrates the material capacitance according to the digital moisture signals and the comparison table. Thereof the processor 42 can calculate the material level by the RF admittance according to the calibrated material capacitance and the digital level signal.

Figure 2:
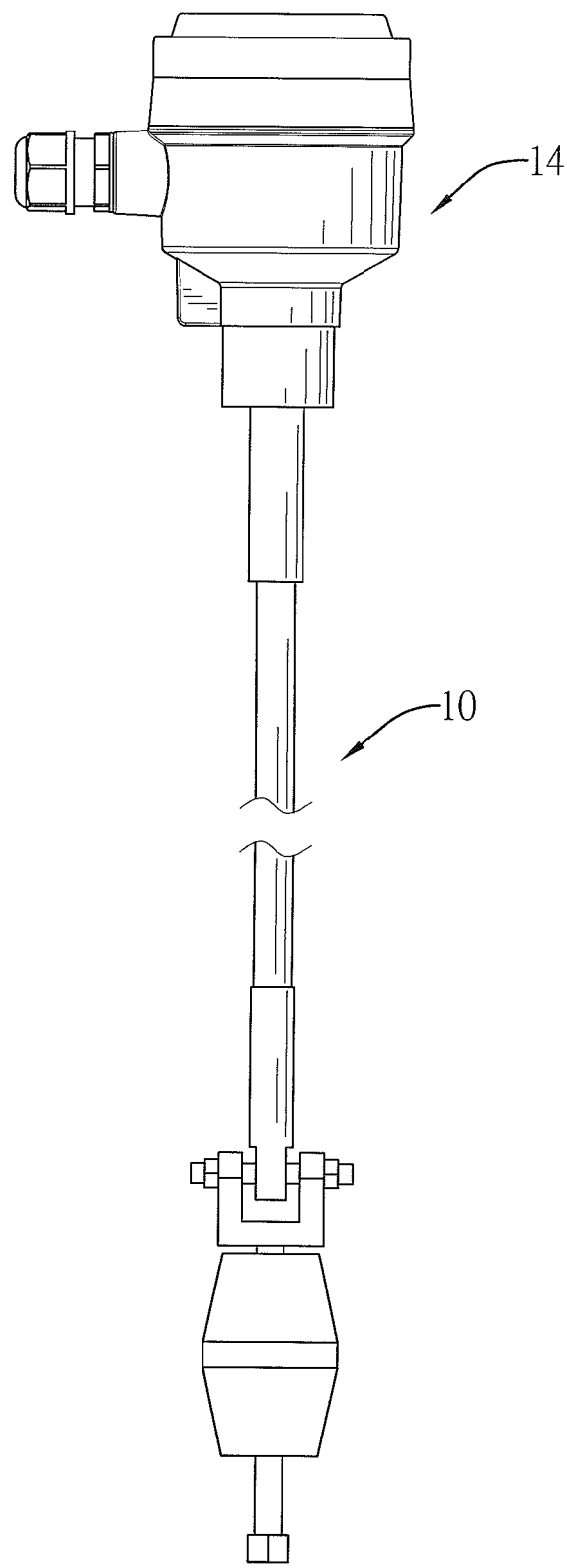
FIG. 2 is a side view of the measurement device of FIG. 1.
Figure 3:
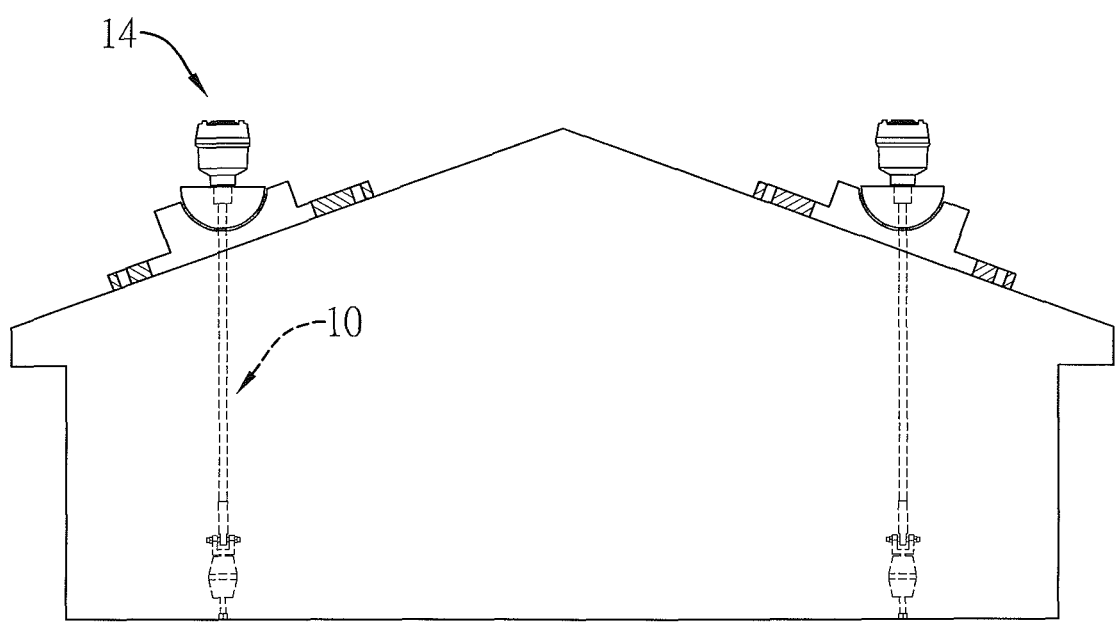
FIG. 3 is a schematic diagram for embodiments of the measurement device of FIG. 2 adapted to a silo.

With reference to FIG. 2, a box 14 is mounted at a terminal of the cable. The box 14 comprises a printed circuit board (PCB) (not shown in figures), and the PCB comprises the foregoing modules. With reference to FIG. 3, the box 14 is mounted on a roof of a silo, and the cable 10 is dropped into the silo with the other terminal of the cable 10 fixed on a bottom of the silo. Therefore, the cable 10 can detect the material level regardless of amount of the material.

Figure 5A:
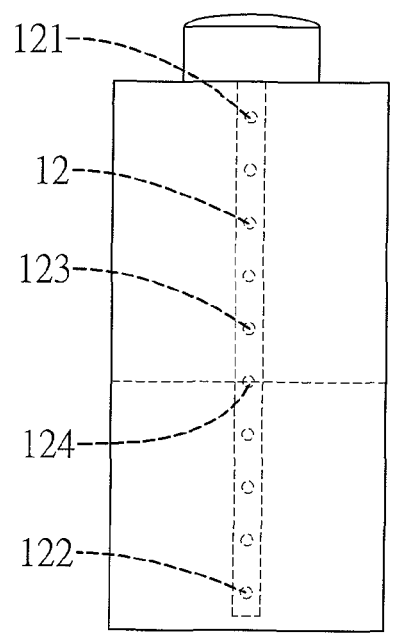
FIG. 5A is a schematic diagram of a silo with the measurement device of FIG. 1 and with a small amount of material stored in the silo.
Figure 5B:
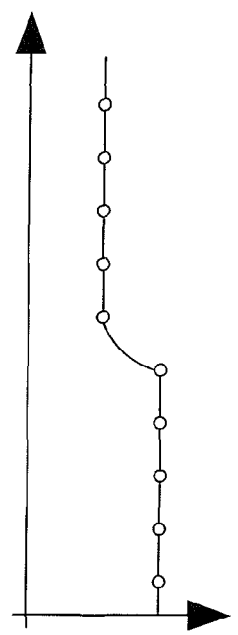
FIG. 5B is a line diagram for temperatures and material level of FIG. 5A.
Figure 6A:
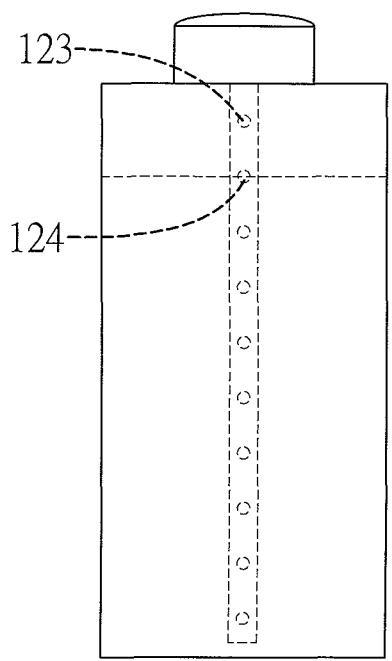
FIG. 6A is a schematic diagram of a silo with the measurement device of FIG. 1 and with a large amount of material stored in the silo.
Figure 6B:
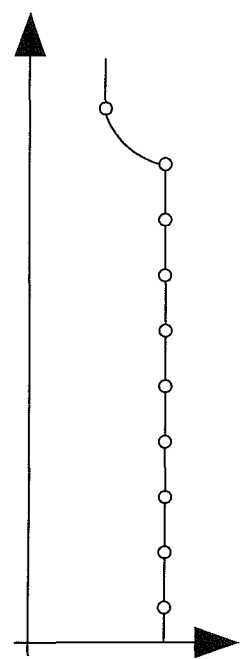
FIG. 6B is a line diagram for temperatures and material level of FIG. 6A.

With reference to FIGS. 5A and 5B, the processor 42 of the measurement device further determines a temperature difference between two different substances. In other words, the temperature sensed by the thermal sensing units 12 exposed from the material is different from the temperature sensed by the thermal sensing units 12 immersed in the material. The different substances have different thermal conductivities. Therefore, the temperature difference can be detected at a junction between two different substances.

For example, the temperature difference can be detected at a junction between the air and the water because of different thermal conductivity coefficients of the two different substances.

An ADC of a conventional measurement device can execute an analog to digital conversion in full range. For example, a 12-bits ADC can convert an analog signal to a digital signal represented by 4096 different levels, and the full range is converted to 4096 different levels. When a user wants to increase a resolution of the analog to digital conversion, the user needs to replace the original ADC with a high resolution ADC.

The ADCs of the measurement device can select any range of the measurement device for analog to digital converting. A junction of two different substances can be determined when the temperature difference is detected. The two thermal sensing units 12 closest to the junction can be determined. The ADCs can only process the range between any two designated thermal sensing units 12, instead of processing a range between the first and the last thermal sensing units 12. On the other hand, range processed by the ADCs can be reduced, and accuracy of the analog to digital conversions can be raised without increasing the resolution of the ADCs.

Figure 4A:
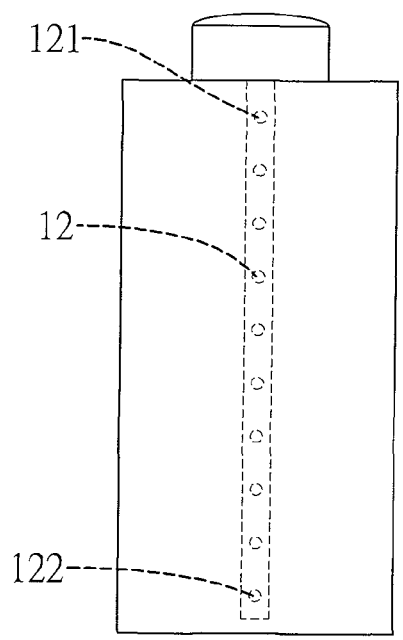
FIG. 4A is a schematic diagram of a silo with the measurement device of FIG. 1 and without materials stored in the silo.
Figure 4B:
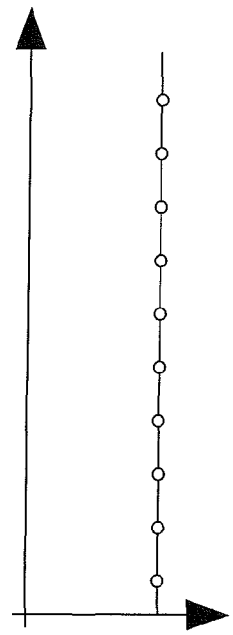
FIG. 4B is a line diagram for temperatures and material level of FIG. 4A.

With reference to FIGS. 4A and 4B, for example, the first ADC 22 can select a range between a first thermal sensing unit 121 and a second thermal sensing unit 122. Resolution of the first ADC 22 is 16-bits. The first ADC 22 can encode the range to one in 65536 different levels. A first capacitance sensed by the first thermal sensing unit 121 is 870 pf, and a second capacitance sensed by the second thermal sensing unit 122 is 500 pf. Accuracy of this analog to digital conversion is $(870-550)/2^{16}$.

With reference to FIGS. 5A, 5B, 6A and 6B, the first ADC 22 of the measurement device selects a new range according to the temperature difference. The new range is between a third thermal sensing unit 123 and a fourth thermal sensing unit 124. The third thermal sensing unit 123 and the fourth thermal sensing unit 124 are the closest to the junction of two different substances. The resolution of the first ADC 22 is not changed. The first ADC 22 can only encode the new range to one in 65536 different levels. A third capacitance sensed by the third thermal sensing unit 123 is 750 pf, and a fourth capacitance sensed by the fourth thermal sensing unit 124 is 550 pf. Accuracy of this analog to digital conversion is $(750-550)/2^{16}$. The accuracy of this analog to digital conversion is raised. On the other hand, the measurement device of the present invention can use the original ADC to obtain high accuracy as provided by a high resolution ADC.

The material capacitance is an important parameter when calculating the material level by the RF admittance. The material capacitance changes with the temperature or the moisture of the material. Therefore, the measurement device of the present invention can calibrate the material capacitance according to the temperature and the moisture of the material. Then, the processor 42 calculates the material level according to the calibrated material capacitance and the RF admittance.

A relationship between the material capacitance and the temperature or the moisture of the material may be a positive correlation or a negative correlation. The positive correlation indicates that when the temperature or the moisture of the material increases, the material capacitance also increases. The negative correlation indicates that when the temperature or the moisture of the material increases, the material capacitance decreases. The relationship between the material capacitance and the temperature or the moisture of the material may be linear or nonlinear.

In the measurement device of the present invention, the ADCs of the measurement device can select a range for analog to digital converting according to the temperature difference. Therefore, accuracy of the ADC can be raised without replacing the original ADC with a high resolution ADC.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:

1. A measurement device for detecting a material level and a temperature comprising:

a cable having an electrode and a plurality of thermal sensing units that are mounted on the cable and separated from each other;

a level sensing module electronically connected with the electrode and outputting a wave signal to the electrode for generating radio frequency (RF) admittance and outputting a level signal;

a thermal sensing module electronically connected with the thermal sensing units and outputting a thermal signal;

a processing module having a storage unit and a processor, wherein the storage unit is electronically connected with the processor and stores a reference table, wherein the reference table comprises temperatures and material capacitances; and wherein the processor is electronically connected with the level sensing module and the thermal sensing module for receiving the level signal and the thermal signal; the processor determines a material capacitance according to the level signal; the processor refers to the reference table to calibrate the material capacitance based on the thermal signal to obtain a calibrated material capacitance; the processor calculates the material level by the RF admittance according to the calibrated material capacitance and the level signal; and a power module electronically connected with the cable, the level sensing module, the thermal sensing module, and the processing module.

2. The measurement device as claimed in claim 1, wherein the level sensing module further has a level signal processor and a waveform producing unit;

wherein the level signal processor is electronically connected to the electrode;

wherein the waveform producing unit is electronically connected between the electrode and the processor, and produces the wave signal.

3. The measurement device as claimed in claim 2, further comprising:
a moisture sensing module having a moisture signal processor and a third ADC;
wherein the cable further has a plurality of moisture sensing units, and the moisture sensing units are mounted on the cable and separated from each other; and
wherein the moisture signal processor is electronically connected with the moisture sensing units and the third ADC, and the third ADC is electronically connected with the processor.

4. The measurement device as claimed in claim 3, wherein the storage unit further stores a comparison table; and
the comparison table comprises moistures and material capacitances.

5. The measurement device as claimed in claim 2, wherein the level sensing module further has an isolated signal processor and an analog signal isolator;
wherein the isolated signal processor is electronically connected between the electrode and the analog signal isolator; and
wherein the analog signal isolator is electronically connected with the level signal processor and the waveform producing unit.

6. The measurement device as claimed in claim 1, wherein the thermal sensing module has a thermal signal processor and a second ADC;
wherein the thermal signal processor is electronically connected with the thermal sensing units and the second ADC; and
wherein the second ADC is electronically connected with the processor.

7. The measurement device as claimed in claim 6, further comprising:
a moisture sensing module having a moisture signal processor and a third ADC;
wherein the cable further has a plurality of moisture sensing units, and the moisture sensing units are mounted on the cable and separated from each other; and
wherein the moisture signal processor is electronically connected with the moisture sensing units and the third ADC, and the third ADC is electronically connected with the processor.

8. The measurement device as claimed in claim 7, wherein the storage unit further stores a comparison table; and
the comparison table comprises moistures and material capacitances.

9. The measurement device as claimed in claim 6, wherein the thermal sensing module further has a digital signal isolator, and the digital signal isolator is electronically connected between the second ADC and the processor.

10. The measurement device as claimed in claim 9, wherein the thermal sensing module further has a switching unit, and the switching unit is electronically connected with the thermal sensing units and the digital signal isolator.

11. The measurement device as claimed in claim 1, further comprising:
a moisture sensing module having a moisture signal processor and a third ADC;
wherein the cable further has a plurality of moisture sensing units, and the moisture sensing units are mounted on the cable and separated from each other; and
wherein the moisture signal processor is electronically connected with the moisture sensing units and the third ADC, and the third ADC is electronically connected with the processor.

12. The measurement device as claimed in claim 11, wherein the storage unit further stores a comparison table; and
the comparison table comprises moistures and material capacitances.

13. The measurement device as claimed in claim 1, wherein the cable is a steel wire rope.

14. The measurement device as claimed in claim 1, wherein the thermal sensing units are one-wire digital thermometers, resistance thermometers (RTDs), or thermocouples.

15. The measurement device as claimed in claim 1, further comprising an output module, and the output module is electronically connected with the processor.

* * * * *